United States Patent [19]

Böhm

[11] 4,152,117

[45] May 1, 1979

[54] PROCESS FOR THE QUANTITATIVE ANALYSIS OF ORGANOALUMINUM COMPOUNDS IN THEIR SOLUTIONS

[75] Inventor: Ludwig Böhm, Mainz, Fed. Rep. of Germany

[73] Assignee: Hoechst Aktiengesellschaft, Frankfurt am Main, Fed. Rep. of Germany

[21] Appl. No.: 881,912

[22] Filed: Feb. 28, 1978

[30] Foreign Application Priority Data

Mar. 2, 1977 [DE] Fed. Rep. of Germany ....... 2709009

[51] Int. Cl.² ............................................ G01N 25/20
[52] U.S. Cl. ................................ 23/230 R; 23/230 M; 422/51
[58] Field of Search ............. 23/230 R, 253 R, 230 M

[56] References Cited

U.S. PATENT DOCUMENTS 3,160,477   12/1964   Wasilewski ........................ 23/253 R

OTHER PUBLICATIONS

Everson et al., Anal. Chem., "Determination of Alkylaluminum Compounds by Thermometric Titration," vol. 37, pp. 806-811, (1965).

Primary Examiner—R. E. Serwin
Attorney, Agent, or Firm—Curtis, Morris & Safford

[57] ABSTRACT

The concentration of organoaluminum compounds in their solutions can be determined quantitatively, even in a range of less than 10 mmols/dm³, when adding to the solution to be analyzed instantaneously an excess of reactant and when measuring the produced reaction heat.

2 Claims, 4 Drawing Figures

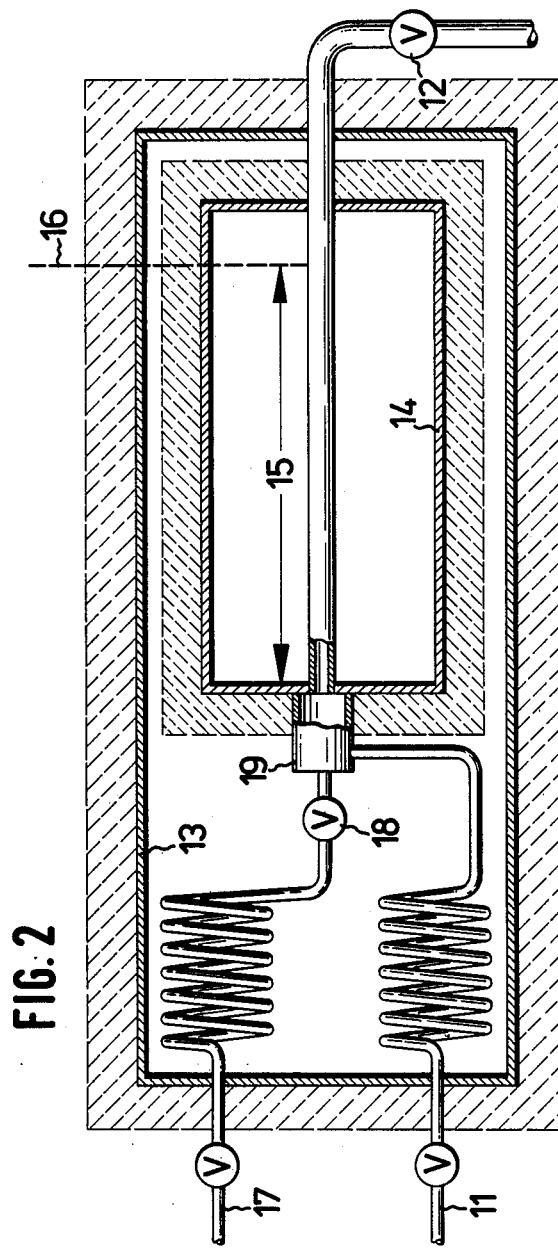

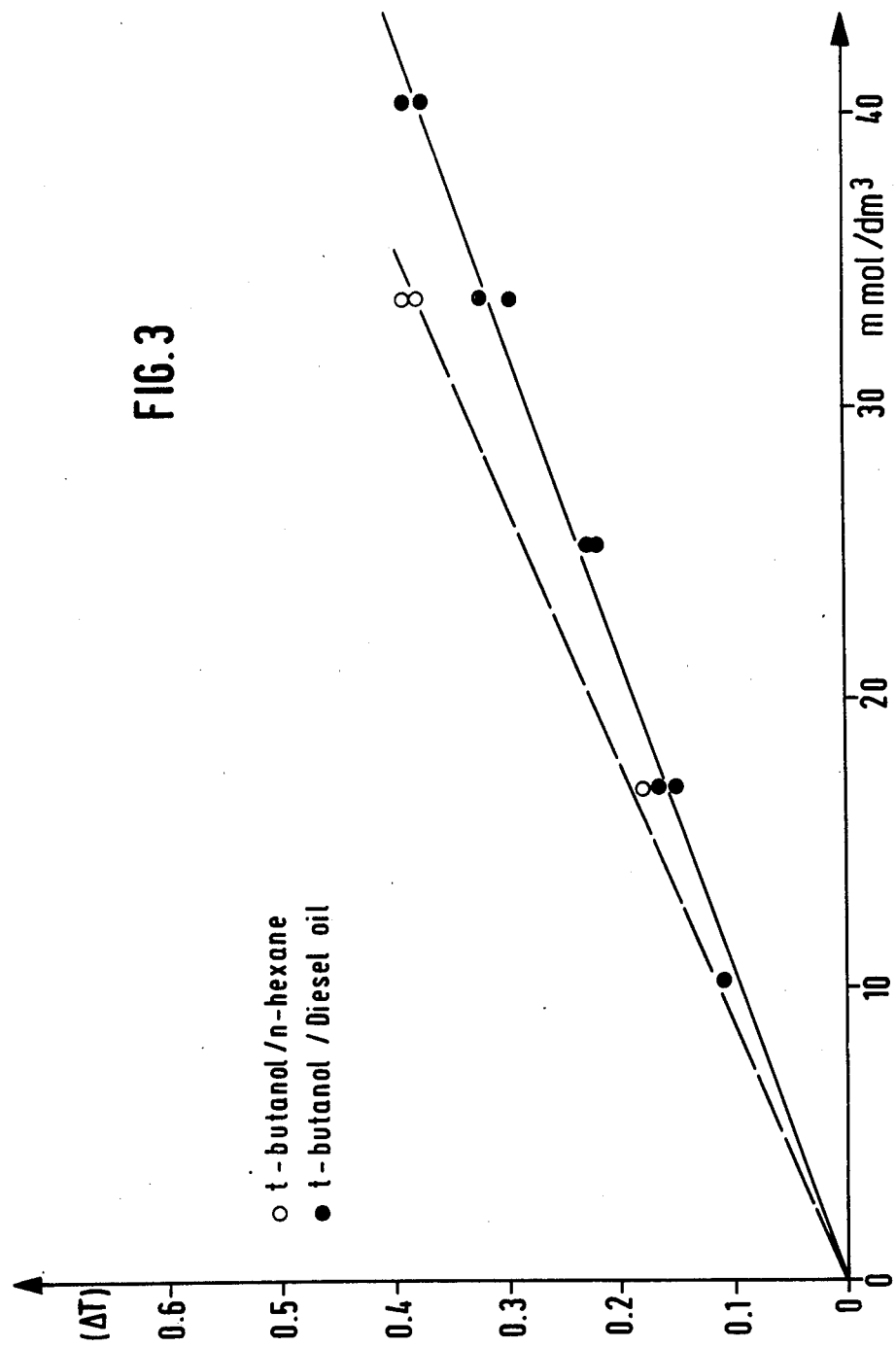

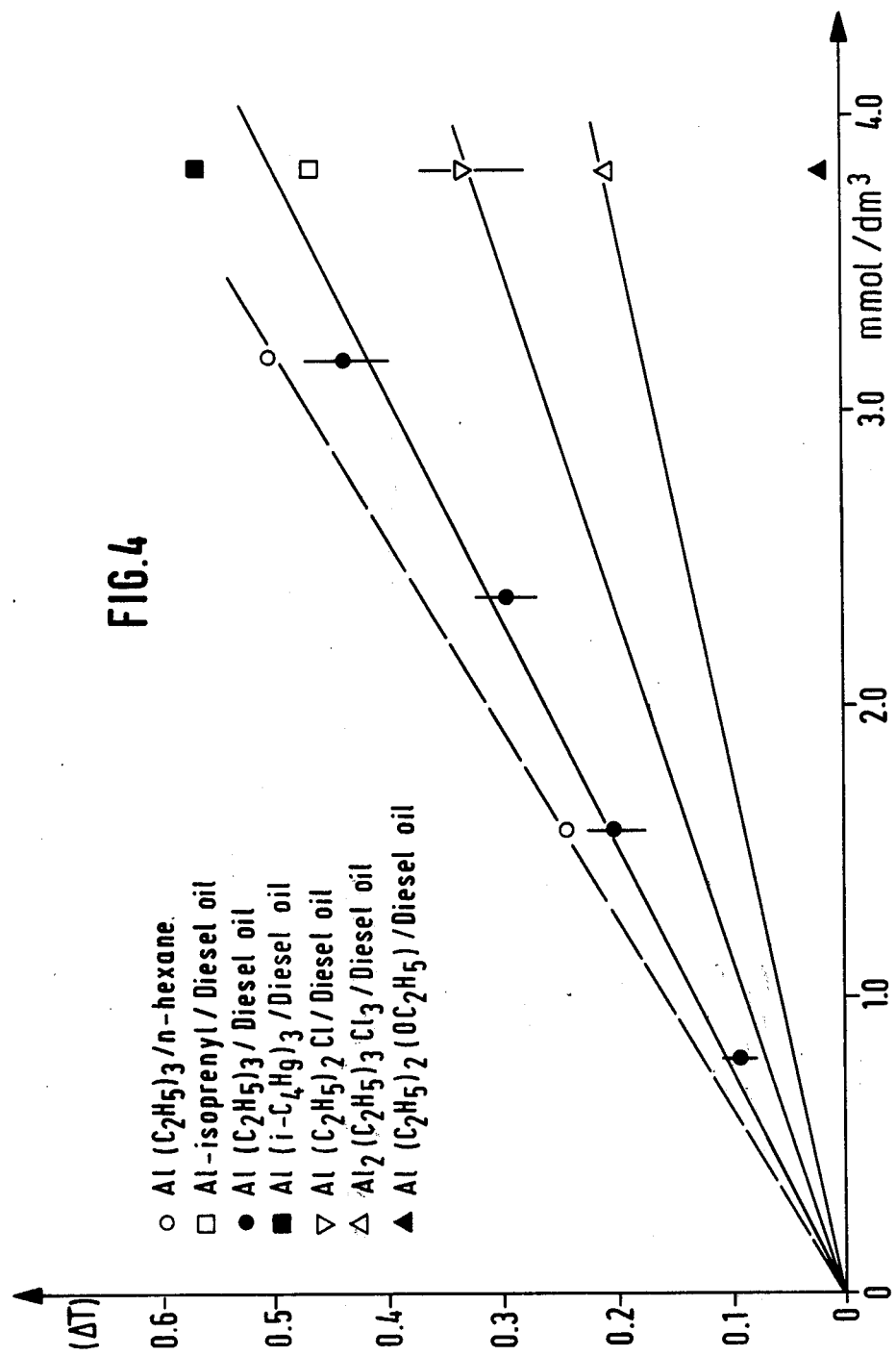

PROCESS FOR THE QUANTITATIVE ANALYSIS OF ORGANOALUMINUM COMPOUNDS IN THEIR SOLUTIONS

The invention relates to the quantitative analysis of organoaluminum compounds in their solutions.

There are several industrially interesting processes in which organoaluminium compounds are used as catalysts or as co-catalysts, for example the low pressure polymerization of 1-olefins according to the methods of Ziegler and Natta, in which the organoaluminum compounds are usually present in relatively low concentrations of less than 10 mmols/dm$^3$. It is of considerable interest for the profitability and reproducibility of the processes that the quantity of the dissolved organoaluminum compounds, in this concentration range, be determined quantitatively and be continuously measured automatically.

A number of processes have been proposed for the quantitative analysis of organoaluminum compounds.

Thus the concentration may be determined by measuring photometrically the concentration of organoaluminum complexes with suitable substances, for example isoquinoline.

Furthermore processes are known which comprise conductometric or potentiometric measuring methods or in which the dielectric coefficient is measured. Finally it is known to measure the reaction heat produced during the reaction of certain reactants with organoaluminum compounds and to utilize it for thermometric titration methods (cf. W. L. Everson and Evelyn M. Ramirez, Analytical Chemistry 37, 806–811, (1965)). In a known process of this kind, for example, organoaluminum compounds such for example as Al(CH$_3$)$_3$, AlH(CH$_3$)$_2$, Al(C$_2$H$_5$)$_3$, AlH(C$_2$H$_5$)$_2$, Al(n-C$_3$H$_7$)$_3$, Al(i-C$_3$H$_7$)$_3$, Al(n-C$_4$H$_9$)$_3$, Al(i-C$_4$H$_9$)$_3$, AlH(i-C$_4$H$_9$)$_3$, AlH(i-C$_4$H$_9$)$_2$, (CH$_3$)$_2$AlCl, (C$_2$H$_5$)$_2$AlCl, (C$_2$H$_5$)AlCl$_2$ and others are titrated in toluene solution with various ethers, amines, ketones and alcohols, particularly with di-n-butyl ether, t-butanol, triethylamine and isoquinoline. The heat produced is converted into electric signals by means of a thermistor, which signals are then traced by a recorded. It becomes evident in this method that first only one molecule of the reactant reacts with the organoaluminum compound, which means that the reaction stops at the stage of the 1:1 reaction product, independent of the concentration of the organoaluminum compound. When using a monohydric alcohol, an Al-C bond is converted into an Al-O-C bond, whereas when using amines and ethers, 1:1 complex compounds are formed and no bonds are split off. When using alcohols, the reaction stops at the stage of the 1:1 reaction products only when the alcohols used are tertiary alcohols for example t-butanol. When using tertiary amines, for example triethylamine and pyridine and furthermore ethers, for example tetrahydrofurane, there are formed 1:1 complex compounds. Among the aforesaid reactants t-butanol is the most suitable compound since in this case the reaction enthalpy is the best.

The indicated reactions proceed successfully when using trialkyl compounds for example Al(C$_2$H$_5$)$_3$, alkyl chlorides, for example Al(C$_2$H$_5$)$_2$Cl and alkylhydrides, for example Al(C$_2$H$_5$)$_2$H, whereas they do not take place when using dialkylalkoxy compounds, for example Al(C$_2$H$_5$)$_2$(OC$_2$H$_5$). All of the aforesaid compounds are present as solutions in hydrocarbons, for example n-hexane or diesel oil.

The described processes can be performed with sufficient accuracy only at concentrations of more than 10 mmols/dm$^3$, because during the slowly proceeding titration disturbing temperature effects may occur with affect the measured value. In order to avoid effects of this kind, a very high technical expenditure would be necessary. For this reason the described titration process cannot be applied without high expenditure to the quantitative analysis or organoaluminum compounds at concentrations of less than 10 mmols/dm$^3$ which are found during the low pressure polymerization of olefins according to the method of Ziegler and Natta.

It has now been found that organoaluminum compounds can be analyzed quantitatively at concentrations of this low range when adding to the solution to be tested instantaneously an excess of reactant and when measuring thereafter the reaction heat produced.

The present invention, consequently, provides a process for the quantitative analysis of dissolved organoaluminum compounds by reacting them with a tertiary alcohol, a tertiary amine or an ether, which comprises adding to the solution of the organoaluminum in one step in excess of the tertiary alcohol, the tertiary amine or the other and measuring the reaction heat produced. In this process a heat exchange with the exterior cannot occur owing to the construction of the reaction vessel.

The process according to the invention is applicable to the quantitative analysis of aluminum trialkyls, aluminum alkyl chlorides, aluminum alkyl hydrides and of reaction products of aluminum trialkyls or aluminum dialkyl hydrides with diolefins. Examples of these compounds are:

Al(CH$_3$)$_3$, Al(C$_2$H$_5$)$_3$, Al(n-C$_3$H$_7$)$_3$, Al(i-C$_3$H$_7$)$_3$, Al(n-C$_4$H$_9$)$_3$, Al(i-C$_4$H$_9$)$_3$, Al(C$_6$H$_{13}$)$_3$, Al(C$_8$H$_{17}$)$_3$, AlH(CH$_3$)$_2$, AlH(C$_2$H$_5$)$_2$, AlH(n-C$_3$H$_7$)$_2$, AlH(i-C$_3$H$_7$)$_2$, AlH(n-C$_4$H$_9$)$_2$, AlH(i-C$_4$H$_9$)$_2$, AlH(C$_6$H$_{13}$)$_2$, AlH(C$_8$H$_{17}$)$_2$, (CH$_3$)$_2$AlCl, (CH$_3$)$_2$AlCl, (CH$_3$)AlCl$_2$, (C$_2$H$_5$)$_2$AlCl, (C$_2$H$_5$)AlCl$_2$, (n-C$_3$H$_7$)$_2$AlCl, (i-C$_3$H$_7$)AlCl$_2$, (i-C$_4$H$_9$)$_2$AlCl, (n-C$_4$H$_9$)AlCl$_2$, (C$_2$H$_5$)$_3$Al$_2$Cl$_3$, (n-C$_3$H$_7$)$_3$Al$_2$Cl$_3$, (i-C$_4$H$_9$)$_3$Al$_2$Cl$_3$, Al-isoprenyl.

The organoaluminum compounds to be determined are present in a dissolved state. Preferably the solvent is an aliphatic or aromatic hydrocarbon, for example pentane, hexane, heptane, octane, decane, cyclohexane, benzene, toluene, xylene, cumene, or mineral oil fractions which have been liberated from oxygen or sulfur by hydrogenation, for example purified diesel oil.

Examples of preferred tertiary alcohols are t-butanol, t-amyl alcohol or t-hexanol, t-butanol being most preferred. Examples of tertiary amines are triethylamine, triethylamine, tri-n-propylamine, tri-i-propylamine, N,N-dimethylcyclohexylamine, pyridine and isoquinoline, triethylamine being the preferred amine. Suitable ethers are diethyl ether, di-n-propyl ether, di-i-propyl ether, di-n-butyl ether, di-i-amyl ether and dicyclohexyl ether. Among the aforesaid solvents t-butanol is the most preferred compound.

Since the reactions stop at the stage of the 1:1 reaction product, the reaction enthalpy is directly proportional to the molar number of the organoaluminum compound and, consequently, for a predetermined volume of the solution, to the concentration. Thus, the change of temperature occuring when performing the reaction adiabatically is directly proportional to the concentration of the organoaluminum compound. This change of the temperature may be measured with great accuracy. During the evaluation it has to be taken into account that an enthalpy may occur when mixing the reactant with the solvent. When mixing, for example, t-butanol with hydrocarbons, the system is cooled (negative mixing enthalpy).

The process can be employed in a concentration range of from 0.05 to 100 mmols/dm$^3$ of the organoaluminum compound, preferably in a range of from 0.1 to 10 mmols/dm$^3$. The reactant is added in one step to the solution to be analyzed in a 20- to 100-fold amount of the concentration of the organoaluminum compound to be expected.

The process can be performed using an analyzer operating both periodically or continuously or using a flow apparatus, the reactant being injected into the latter continuously or periodically.

The invention will be illustrated with reference to the accompanying drawings.

FIG. 2 is a view in cross section of the flow apparatus; and

FIGS. 3 and 4 are graphs.

Figure 1:
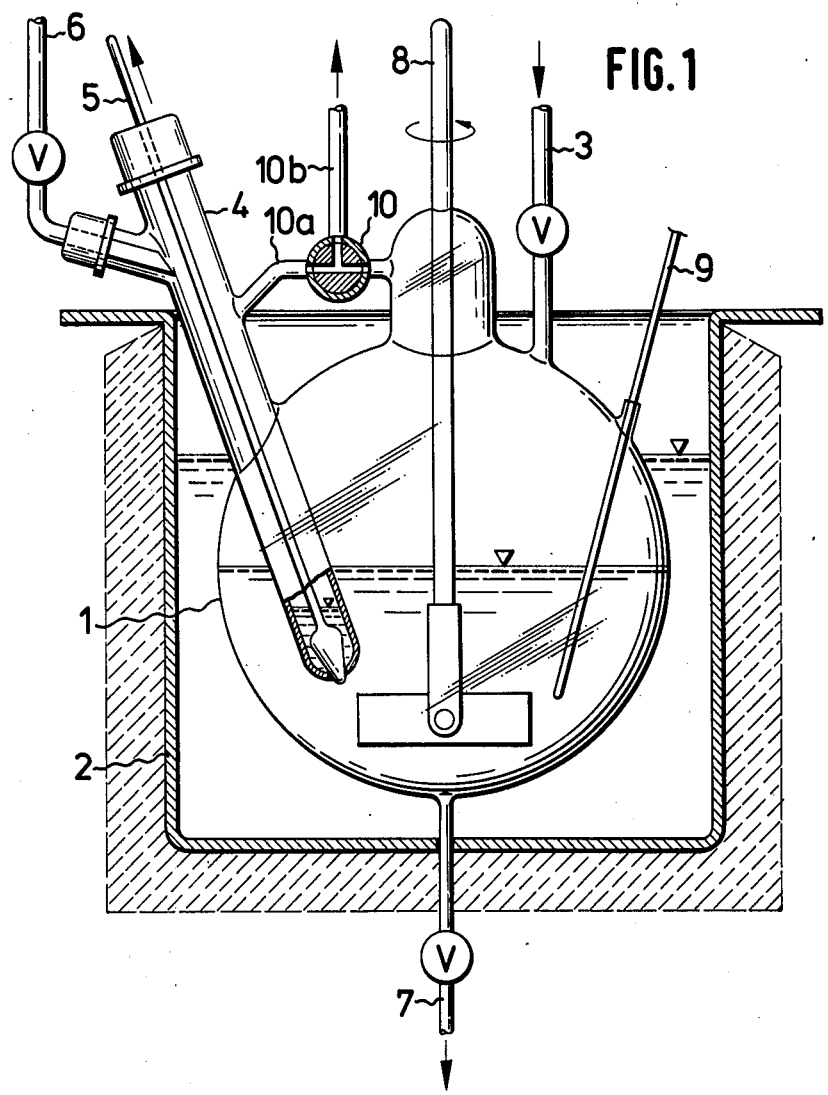
FIG. 1 is a view, partly in cross section, of an analyzer.

The analyzer working periodically or continuously according to the FIG. 1 is composed of a reaction vessel 1, which is made from thick-walled glass and which is located in a precision thermostate 2. by the inlet 3 the solution of the organoaluminum compound is fed to the reaction vessel in a predetermined volume under protective gas (N$_2$, Ar). The protective gas escapes via the conduits 10a and 10b.

The reactant, for example t-butanol, is fed to the reaction vessel 4 via the inlet 6 under protective gas, in a predetermined volume. Both components are slightly heated while stirring in the reaction vessel 1 with a stirrer 8. The temperature oscillations have to be at most of about 0.002 K.

When a constant temperature has set up, both components are mixed by pulling the plunger 5 upwards. The change of temperature occurring thereby is measured, for example with a "Negative-Temperature-Coefficient"-resistor (NTC-resistor) 9.

Upon measuring, the contents of the vessel are withdrawn via the conduit 7. Thereafter the vessel 4 is rinsed with the reactant and subsequently the vessel 1 is rinsed with the next solution to be analyzed. Thereafter the cycle starts again.

The three-way cock 10 and the conduits 10a and 10b serve for compensating the pressure.

Through the flow apparatus according to FIG. 2 the solution of the organoaluminum compound is continuously pumped via the conduit 11 and it scapes through the valve 12. It is heated to the measuring temperature in the thermostate 13.

The conduits in the apparatus are made from metal in order to insure a good heat transmission. Inside of the thermostate 13 is located a chamber 14 which is surrounded by heat insulating walls. In this chamber takes place the reaction between the organoaluminum compound and the reactant in the zone 15. The temperature increase is measured at the position 16 with a NTC-resistor. The reactant is pumped into the apparatus in non-diluted state via the conduit 17. It is first heated to the measuring temperature and is then mixed continuously or periodically with the solution of the organoaluminum compound at a ratio of 1:300 in the mixing chamber 19 by opening and closing the injection valve 18. The flow velocity must be adapted to the length of the zone 15 in such a way that the time required for passing through this zone corresponds approximately to 10 half-times of the chemical reaction.

The advantage of the process of the invention resides in the fact that the concentration of the organoaluminum compounds can be determined rapidly and with high accuracy even at a range of less than 10 mmols/dm$^3$ and that the process is applicable to continuous automatic checking of production processes.

The following examples illustrate the invention:

EXAMPLES

Measurings are performed in an analysis apparatus shown in FIG. 1 according to the described processes. In the tests the organoaluminum compounds $Al(C_2H_5)_3$, $Al(i-C_4H_9)_3$, Al-isoprenyl (reaction product of an aluminum trialkyl or of a dialkylaluminum hydride with isoprene), $Al(C_2H_5)_2Cl$, $Al_2(C_2H_5)_3Cl_3$ and $Al(C_2H_5)_2(OC_2H_5)$ in a hydrocarbon (n-hexane) or in a mixture of hydrocarbons (diesel oil) are first given into the apparatus and the reactant added to this solution (300 cm$^3$) is t-butanol (1 cm$^3$).

First pure t-butanol is added only to the solvent in order to measure the temperature effect occurring. The mixing process is an endothermal processes, that is to say that the temperature diminuishes in the system. In FIG. 3 the absolute values of this change of temperature are plotted as a function of the concentration of the added t-butanol.

When adding t-butanol in excess (33.5 mmols/dm$^3$) to the solution containing an organoaluminum compound, the temperature changes as a consequence of the exothermal reaction. According as the reaction heat is higher, lower or equal to the heat of mixing, the measured change of temperature is positive, negative or zero. In FIG. 4 the changes of the temperature are plotted as a function of the concentration of the organoaluminum compound after having subtracted the change of temperature caused by the mixing processes. It can be distinctly seen that the various organoaluminum compounds show a different behavior. The measured effects are pronounced so that concentrations can be determined with high accuracy.

What is claimed is:

1. Process for the quantitative analysis of organoaluminum compounds of aluminum trialkyls, aluminum alkyl chlorides, aluminum alkyl hydrides or of reaction products of aluminum trialkyls or aluminum dialkyl hydrides with diolefin in solutions by reacting the same with a tertiary alcohol, a tertiary amine or an ether, which comprises adding in a concentration, in said solution, from 0.05 to 100 m mols/dm$^3$ in one step to the solution of said organoaluminum compound an excess of the tertiary alcohol, the tertiary amine or an ether as a reactant with said organoaluminum compound in a ratio of reactant to organoaluminum compound of 20:1 to 100:1 and measuring the change of temperature occurring in a reaction zone being substantially heat exchange proof with the environment.

2. Process as claimed in claim 1, which comprises carrying out the reaction in a continuously working flow calorimeter zone.

* * * * *